(12) United States Patent
Winstrom et al.

(10) Patent No.: US 6,761,899 B1
(45) Date of Patent: Jul. 13, 2004

(54) PARTICULATE ANIMAL FEED SUPPLEMENTS AND PROCESSES FOR THE PREPARATION THEREOF

(75) Inventors: Andrew Lee Winstrom, Omaha, NE (US); Willis L. Winstrom, Omaha, NE (US)

(73) Assignee: Pennfield Oil Company, Omaha, NE (US)

( * ) Notice: Subject to any disclaimer, the term of this patent is extended or adjusted under 35 U.S.C. 154(b) by 0 days.

(21) Appl. No.: 09/350,474

(22) Filed: Jul. 9, 1999

Related U.S. Application Data

(60) Provisional application No. 60/115,761, filed on Jan. 13, 1999, provisional application No. 60/105,229, filed on Oct. 21, 1998, and provisional application No. 60/103,074, filed on Oct. 5, 1998.

(51) Int. Cl.[7] ........................... A23K 1/17; A61K 31/65
(52) U.S. Cl. ..................... 424/442; 424/438; 424/409; 424/410; 514/152
(58) Field of Search .................. 426/635; 424/442, 424/438, 409, 417, 421, 410, 420, 115.7, 116; 514/152, 153

(56) References Cited

U.S. PATENT DOCUMENTS

| | | |
|---|---|---|
| 2,516,080 A | 7/1950 | Sobin et al. .................. 167/65 |
| 3,696,189 A | 10/1972 | Snyder ........................ 424/38 |
| 4,081,527 A | 3/1978 | Armstrong et al. ........... 424/80 |
| 4,211,781 A | 7/1980 | Chapman .................... 424/250 |
| 4,447,421 A | 5/1984 | Klothen ...................... 424/227 |
| 5,182,126 A | 1/1993 | Vinci et al. .................... 426/74 |
| 5,266,347 A | 11/1993 | King .......................... 426/623 |
| 5,374,425 A | 12/1994 | Porter ...................... 424/93.45 |
| 5,466,469 A | 11/1995 | Kuhrts ........................ 424/451 |
| 5,589,186 A | 12/1996 | Isobe et al. ................. 424/438 |
| 5,641,511 A | 6/1997 | Kuhrts ........................ 424/451 |
| 5,908,634 A * | 6/1999 | Kemp et al. ................. 424/442 |
| 6,506,402 B1 * | 1/2003 | Winstrom .................... 424/442 |

FOREIGN PATENT DOCUMENTS

| | | | |
|---|---|---|---|
| DE | | 138273 | * 10/1979 |

OTHER PUBLICATIONS

Feeds and Feed Additives, Nonruminant Feeds; Park W. Waldroup, University of Arkansas; http://jws–edck.wiley-.com:8095/articles/nonrwald.a01/sect1_4.html; Dec. 5, 2001.

* cited by examiner

*Primary Examiner*—Neil S. Levy
(74) *Attorney, Agent, or Firm*—Suiter West PC LLO

(57) ABSTRACT

A medicated animal feed additive in a solid particulate or granular form having improved resistance to powdering and good fracture toughness is provided. The animal feed additive according to the present invention does require a compression or compacting step to achieve its solid structural form. The present invention also provides a method of producing animal feed compositions. In a further embodiment, the present invention relates to a method of combating microbial infection in animals comprising orally administering to said animals a prophylactic or therapeutic amount of an animal comestible composition comprising a medicated feed supplement according to the present invention.

15 Claims, 4 Drawing Sheets

PARTICULATE ANIMAL FEED SUPPLEMENTS AND PROCESSES FOR THE PREPARATION THEREOF

RELATED APPLICATIONS

This application claims priority under 35 U.S.C. § 119(e) to the following U.S. Provisional Applications: Provisional Application Serial No. 60/103,074, filed Oct. 5, 1998; Provisional Application Serial No. 60/105,229, filed Oct. 21, 1998; and Provisional Application Serial No. 60/115,761, filed Jan. 13, 1999. The entire contents of all of the above applications are incorporated herein by reference.

FIELD OF THE INVENTION

The present invention relates to particulate or granular medicated animal feed supplements and methods for making the same.

BACKGROUND OF THE INVENTION

Antibiotics, such as tetracyclines, are used as growth promoters and feed efficiency promoters in animals such as livestock, and for therapeutic and prophylactic disease control in animals such as poultry and livestock, domesticated pets, and so forth. Such antibiotics are typically formulated in an animal feed premix or animal feed supplement containing the antibiotic and an edible carrier. These premixes or animal feed supplements may then be mixed with a sufficient quantity of an appropriate animal feed to provide a final animal feed formulation having the desired level of active compound in the feed.

One problem associated with animal feed medication pertains to the loss of finely divided antibiotics through dusting and electrostatic adhesion of finely divided particles, which may cause a lack of uniformity in drug concentrations in the final feed from batch to batch. Dust particles that adhere to feed mills or other feed processing equipment or that may be carried away in dust collection system may contain significant quantities of the active ingredient. This may cause the feed mixtures to have a lower concentration of the medicament desired. Dust adherent to the feed processing equipment and dust collected in a dust collection that is recycled in subsequent batches may cause the feed mixtures produced in later batches to have a higher concentration of the active ingredient than desired, or may cause carry over of the drug to feed batches which are not intended to contain the drug.

Several attempts have been made to overcome the problem of dust formation in animal feed premixes and supplements. For example, it is known to add oil to reduce the dust and electrostatic adhesion in animal feed supplements. In U.S. Pat. No. 4,211,781, there is taught a process for preparing a substantially dustless carbadox animal feed premix by admixing carbadox with a non-toxic oil and an edible carrier. In U.S. Pat. No. 3,696,189, it is taught to coat the antibiotic particles of an animal feed supplement an oil to stabilize the antibiotic against the deleterious effects of moisture or other materials contained in the animal feed supplement. It is also known to add oil as a pharmaceutically and nutritionally acceptable carrier or diluent for animal feed supplements.

Another attempt to overcome the problem of feed batch cross contamination is taught in U.S. Pat. No. 4,447,421, directed to a process for making particulated animal feed premixes by combining the drug with a compressible carrier, followed by blending the mixture, compressing the mixture, and granulating the composition. Although this process has been somewhat successful in reducing dusting, it would be desirable to reduce dusting further. Attempts have been made to do so through the addition of oil, however, it has been found that the addition of oil causes a loss of structural integrity of such compressed formulations and causes a separation of the drug from the carrier.

It would be desirable to provide an animal feed premix or animal feed supplement which can be prepared directly from a fermentation product without isolating or purifying the antibiotic from the fermentation solids, and which can be prepared in a granular or particulate form without a compression or compaction step, and which does not lose its structural properties upon admixture with oil.

FIG. 4 is a diagrammatic illustration of a prior art method of manufacturing oxytetracycline feed supplements. Oxytetracycline may be formed by a fermentation process, for example, as described in U.S. Pat. No. 2,516,080. The fermentation product comprising the fermentation solids (mycelium) and fermentation liquid are made acidic and the fermentation solids removed from the fermentation broth. The removed solids are discarded and the oxytetracycline may be purified from the liquid by a number of methods. The purified oxytetracycline crystals are typically micron sized (around 600 mesh) and are may be used to form a standardized feed additive by the addition of mineral products, wax, roughage, etc. The final product is a finely divided meal (powder) and is subject to the electrostatic and dusting problems as described above. There is not currently available in the art an animal feed supplement comprising a granular formulation having a relatively large particle size. Therefore, it would also be desirable to provide an oxytetracycline formulation that is granular in nature and of relatively large particle size suitable for use in the veterinary and animal husbandry arts.

SUMMARY OF THE INVENTION

The present invention thus provides medicated animal feed additives in a solid particulate or granular form having improved resistance to powdering and good fracture toughness. The animal feed additive according to the present invention does not require a compression or pressing step to achieve its solid structural form. A dust suppression agent (such as an oil, fat, wax, glyceride, or the like) may optionally be added to bind dust without loss of the structural integrity of the particles. The present invention also provides a method of producing animal feed compositions.

In a further embodiment, there are provided particulate compositions, and methods for making the same, comprising oxytetracycline or chlortetracycline prepared from a fermentation medium and fortified by the addition of pure or semi-pure oxytetracycline or chlortetracycline thereto. As used herein, the term pure or semi-pure oxytetracycline is intended to encompass, the free base, salts of oxytetracycline acceptable for pharmaceutical or veterinary use including acid addition salts, and metal complexes of oxytetracycline and salts thereof, including oxytetracycline calcium complexes. The term pure or semi-pure chlortetracycline is intended to encompass, the free base, salts of chlortetracycline acceptable for pharmaceutical or veterinary use including acid addition salts, and metal complexes of chlortetracycline and salts thereof, including chlortetracycline calcium complexes.

In still a further embodiment, there are provided particulate compositions, and methods for making the same, comprising chlortetracycline prepared from a fermentation medium and fortified by the addition of pure or semi-pure chlortetracycline thereto. In an embodiment, the fermentation medium may further comprise a fermentation residue that has had the antibiotic separated therefrom.

In additional embodiments, the present invention also relates to a method of combating microbial infection in animals comprising orally administering to said animals a prophylactic or therapeutic amount of an animal comestible composition comprising a medicated feed supplement according to the present invention. In yet a further embodiment, the present invention relates to a method for promoting animal growth.

It is to be understood that both the foregoing general description and the following detailed description are exemplary and explanatory only and are not restrictive of the invention as claimed. The accompanying drawings, which are incorporated in and constitute a part of the specification, illustrate an embodiment of the invention and together with the general description, serve to explain the principles of the invention.

BRIEF DESCRIPTION OF THE DRAWINGS

The numerous objects and advantages of the present invention may be better understood by those skilled in the art by reference to the accompanying figures in which.

DETAILED DESCRIPTION OF THE INVENTION

Figure 1:
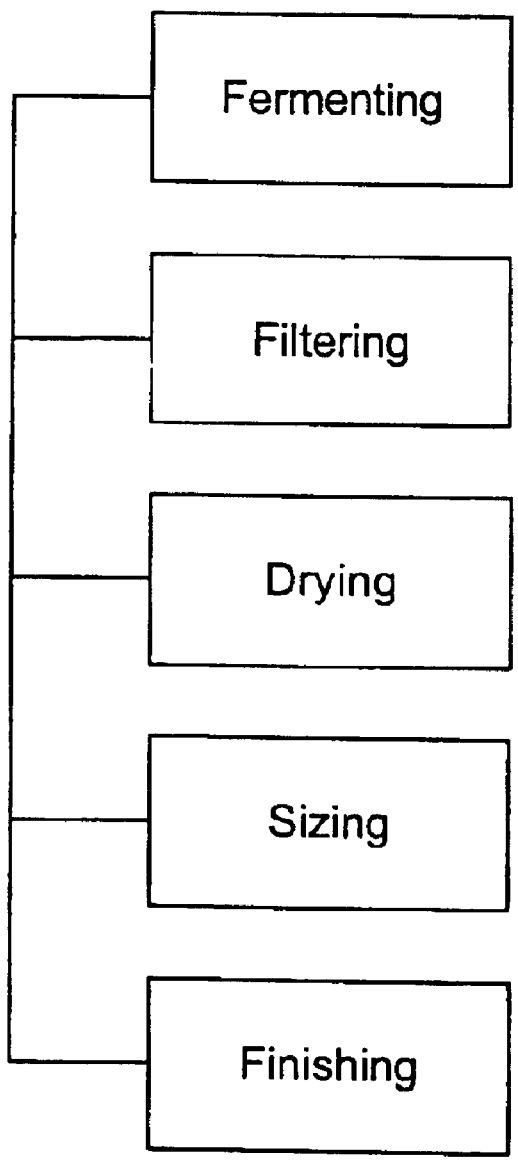
FIG. 1 is a diagrammatic illustration of an exemplary method of manufacturing a particulate animal feed supplement of the present invention.

The animal feed supplements of the present invention comprise an antibiotic containing product of a fermentation process which is further admixed with an edible feed material, mineral product (see attached Appendix "A" of A.F.C.O. "Feed Ingredient Definitions, 57. Mineral Products"), and, optionally, an edible oil. A diagram outlining the process according to the present invention is shown in FIG. 1.

The terms "animal feed premix," "animal feed supplement," and "animal feed additive" are generally used herein interchangeably, without attention to any nuances in meaning, to mean a concentrated additive premix comprising an active ingredient which may be added to an animal's feed to form a medicated comestible composition in accordance with the present invention.

The animal feed supplements according to the present invention may be blended with an animal feed to produce a medicated finished complete or supplement feed product. Animals to which the feed supplements according to the present invention may be administered include pets or companion animals, and ranch or farm animals or other livestock, such as animals raised as a food source or other commercial purpose. Such animals include, but are not limited to, cattle, sheep, horses, pigs, buffalo, goats, dogs, cats, rabbits, rats, mice, minks, fish, and fowl (including egg-laying or edible fowl, such as chickens, turkeys, geese, ducks, quail, pheasant, etc.), and so forth.

The active ingredient may be any antibiotic produced by a fermentation process. Antibiotics produced by fermentation of a microbial source organism are generally known in the art. Examples include, but are not limited to, actinomycin D (*Streptomyces antibioticus*), amphotericin B (*Streptomyces nodosus*), amphomycin (*Streptomyces canus*), antimycin A (Streptomyces sp.), bacitracin (*Bacillus subtilis*), candicidin B (*Streptomyces griseus*), capreomycin (*Streptomyces capreolus*), cephalosporin C (*Cephalosporium acremonium*), cycloheximide (*Streptomyces griseus*), cycloserine (*Streptomyces orchidaceus*), erythromycin (*Streptomyces erythreus*), gentamicin (*Micromonospora purpurea*), gramicidin (*Bacillus brevis*), hygromycin B (*Streptomyces hygroscopicus*), kanarnycin (*Streptomyces kanamyceticus*), lincomycin (*Streptomyces lincolnenis*), mithramycin (Streptomyces sp.), neomycin (*Streptomyces fradiae*), Nystatin (*Streptomyces noursez*), oleandomycin (*Streptomyces antibioticus*), oxytetracyclin (*Streptomyces veamoses*) paromomycin (*Streptomyces rimosus*), benzylpenicillin (penicillin G) (*Penicillium chrysogenum*), phenoxymethylpenicillin (penicillin V) (*Penicillium chrysogenum*), allylmercaptomethylpenicillin (penicillin O) (*Penicillium chrysogenum*), polymyxin B (also colistin) (*Bacillus polymyxa*), streptomycin (*Streptomyces griseus*), tetracycline (*Streptomyces aureofaciens*), 7-chlortetracycline (chlortetracycline) (*Streptomyces aureofaciens*), 7-chloro-6-demethyltetracycline (demeclocycline) (*Streptomyces aureofaciens*), 5-hydroxytetracycline (oxytetracycline) (*Streptomyces rimosus*), thiostrepton (*Streptomyces azureus*), tylosin (*Streptomyces fradiae*), tyrocidine (*Bacillis brevis*), vancomycin (*Streptomyces orientalis*), viomycin (*Streptomyces floridae*), and so forth. In some preferred embodiments, the antibiotic fermentation product is amphotericin B, bacitracin, erythromycin, hygromycin B, tetracycline, chlortetracycline, demeclocycline, oxytetracycline, thiostrepton, or tylosin. In other preferred embodiments, the antibiotic fermentation product is tetracycline, chlortetracycline, demeclocycline, or oxytetracycline. In most preferred embodiments, the antibiotic is chlortetracycline or oxytetracycline.

Tetracyclines are particularly useful because of broad antimicrobial action, with low toxicity, in the therapy of infections caused by gram positive and gram negative bacteria, as well as rickettsiae and the large viruses, such as psittacosis-lymphogranuloma viruses.

The medicated animal final feed mixtures according to the present invention are prepared by adding an animal feed premix prepared in accordance with the present invention to an animal's food. The premix may be added to the food in a number of ways. The feed premix containing a given quantity of active ingredient may be added to a given quantity of feed and mixed or blended to provide a substantially homogeneous medicated feed composition. Large feed lots may be prepared in this manner for treating a large number of animals. Alternatively, feed batches containing feed for a single animal or single meal may be prepared either by mixing a predetermined quantity of premix according to the present invention with the animal feed or by adding a predetermined quantity of premix to an animal's feed as a top dressing.

By varying the quantity of feed supplement added to the feed, the concentration of the active ingredient in the final feed formulation may be adjusted to meet particular needs and may be varied over a wide range. The minimum concentration should be such as to achieve the desired result (therapeutic, prophylactic, growth enhancement, etc.). The maximum concentration should be such as to avoid any undesirable side effects when the feed rations are ingested by the animal. Within these limitations, specific amounts of active ingredient will normally be regulated by the practitioner according to potency of the premix and the usual recommended dosing levels for the active ingredient. The practitioner will generally take into account a number of factors, such as the particular antibiotic, the animal species being treated, the animal's age or stage of development, the frequency of administration, whether the composition is being administered therapeutically or prophylactically and the degree of antimicrobial results sought, the severity of any disease being treated, and so forth. Selecting doses and dosage regimens is generally performed as a routine matter by persons skilled in the arts pertaining to veterinary medicine, animal husbandry, and the like.

In some of the preferred embodiments according to the present invention, the animal feed supplements according to the present invention will contain an antimicrobial concentration ranging from about 10 g/lb to about 300 g/lb, and preferably from about 10 g/lb to about 200 g/lb.

Thus, in formulating the animal comestible feed comprising the animal feed premix according to the present invention to contain the proper amount of active ingredient, one may calculate the amount of active ingredient it is desired to administer to each animal, take into account the amount of feed per day normally consumed by the animal, and compute the proper concentration of antibiotic needed in the feed, and add the appropriate amount of animal premix to achieve the proper concentration of antibiotic in the final product.

In some of the preferred embodiments according to the present invention, the finished feed prepared with the animal feed premix in accordance with the present invention will generally contain the active ingredient in an amount ranging from about from about 10 g/ton to about 3000 g/ton, preferably from about 50 g/ton to about 2000 g/ton, and more preferably, from about 50 g/ton to about 800 g/ton.

As stated above, the, antibiotic is prepared by a fermentation process. The fermentation process may be any suitable fermentation process suitable for the antibiotic being produced and may be a commercial scale fermentation process. Generally, an inoculum of the microbial source organism producing the desired antibiotic is introduced into a fermentation medium to produce a fermentation broth comprising the fermentation medium and inoculum whereby the antibiotic is produced by fermentation in the fermentation broth.

When the concentration of the antibiotic reaches a certain level in the fermentation broth, the fermentation solids are separated from the fermentation broth. The separation may be performed in a number of ways, including pumping the broth through a filter, centrifugation, and so forth. In a preferred embodiment, the fermentations solids are separated by pumping the fermentation broth through a filter press. The wet cake comprising the filtration solids thus produced is dried at elevated temperature until the moisture content reaches from about 3% to about 10%, preferably from about 4% to about 6%. The drying temperature is preferably from about 60° C. to about 90° C., preferably about 80° C. or less.

The dry cake so produced is then sized, for example, by grinding, milling, pulverized, screening, etc., to provide the dried fermentation solids in particulate form without any compression or compaction of the particles. The particles are then screened to produce the crude antibiotic raw material having desired particle size. The particle size ranges from about 180 $\mu$m (80 mesh) to about 2 mm (10 mesh), and is preferably from about 212 $\mu$m (70 mesh) to about 1 mm (18 mesh). In a preferred embodiment, the particles have a size of about 10 mesh or coarser.

As stated above, the animal feed premix according to the present invention comprises an admixture of the dried, sized, antibiotic raw material with an edible feed material, mycelium meal, mineral products, and optionally an oil. In admixing the ingredients, the solid ingredients are preferably admixed, e.g., with a feed blender, by hand, and so forth. When oil is used, the oil is preferably added to the mixture by spraying.

The edible feed material, mineral product, raw antibiotic, and oil are preferably combined in the following concentrations by weight:

| | |
|---|---|
| Edible feed material | 0.0 to 90% |
| Mineral product | 0.0 to 89% |
| Raw fermentation product | 2.4 to 98% |
| Oil or fat | 0.0 to 15% |

In one preferred embodiment, the raw material is assayed and the quantity of edible feed material and mineral product are adjusted to provide a standardized concentration or potency of the antibiotic.

Suitable edible feed materials include grain products such as corn, rice, wheat, milo, rice bran, other straws or grasses rich in crude fibrous material, ground corn cobs, oil seeds and by products, silages, soybean mill run, wheat middlings, wheat bran oat groats, oat bran, barley, alfalfa meal, wheat germ, corn germ meal, soybean grits, corn gluten feed, soybean meal, and rice hulls, or the like. The edible feed material is preferable rice hull.

Any non-toxic oil (or fat), and preferably a nutritive oil, may be used in the formulation of the animal feed premixes according to the present invention. Suitable oils include, for example, mineral oil, waxes, cotton seed oil, peanut oil, corn oil, sesame oil, coconut oil, soybean oil, grapeseed oil, linseed oil, and so forth. The oil is preferably mineral oil.

The mineral product may be any mineral product suitable for use in an animal feed or feed supplement or other veterinary use, such as those listed in Appendix "A." In one embodiment, the mineral product is limestone. By "limestone" is meant not only naturally occurring form calcium carbonate such chalk, dolomite, etc., but also is intended to encompass veterinary, agricultural, and technical grade calcium carbonate. Of course, higher grades of calcium carbonate may be employed as well.

The animal feed premixes according to the present invention may also contain additional ingredients as typically used in animal husbandry, such as coccidiostats, additional antibiotics, minerals, vitamins, growth promoters, antioxidants, anthelmintics, preservatives, colorings, flavorings, or other dietary supplements.

The following Examples are intended to illustrate but not to limit the invention.

EXAMPLES

Raw Materials and Media Composition

A test tube is used to store the spore of the *Streptomyces aureofaciens* chlortetracycline (CTC) strain. Washed sand is screened through an 80 mesh sieve. The sand is placed into a glass tube and sterilized at 121° C., 0.104 Mpa for 30 minutes. After sterilization, the sand is dried and cooled. The strain spore of CTC is inoculated into a sterilized tube containing slant media using an inoculation needle under aseptic conditions. The tube is sealed with a cotton ball. The inoculated media is cultivated for 4–5 days at 30 to 40° C., preferably 35±1° C., under thermostatically controlled conditions. The media is cooled and kept in the refrigerator at 4° C. until ready for use.

Slant Media

The composition of the culture media is as follows:

| Ingredient | Preferred Material | Preferred Range (%) |
|---|---|---|
| Carbon Source | Wheat Bran | 3.0–3.5 |
| Activator | $MgSO_4$ | 0.004–0.006 |
| Nitrogen Source | $(NH_4)_2HPO_4$ | 0.01–0.02 |
| Activator | $K_2HPO_4$ | 0.008–0.012 |
| Solidifier | Agar | 0.05–0.10 |
| Moisturizer | Water | Remainder |

A single colony is selected from cultured media described above under aseptic conditions and inoculated on a slant media as described above. The inoculum is then cultivated for 4–5 days at 30 to 40° C., preferably 35±1° C., under thermostatically controlled conditions. After the growth of the spore, the well-grown slant is selected and kept in a refrigerator at between 3° C. to 5° C. until ready for use.

Seed Media

The composition of the seed media is as follows:

| Ingredient | Preferred Material | Preferred Range (%) |
|---|---|---|
| Carbon Source | Corn Starch | 3.0–4.0 |
| Nitrogen Source | Peanut Meal or Soybean Meal | 1.5–3.5 |
| Nitrogen Source | Peptone | 0.4–0.6 |
| Nitrogen Source | Yeast Powder | 0.4–0.8 |
| Nitrogen Source | $(NH_4)_2SO_4$ | 0.2–0.4 |
| Carbon Source & Buffer | $CaCO_3$ | 0.2–0.4 |
| Activator | NaCl | 0.1–0.3 |
| Activator | $KH_2PO_4$ | 0.02–0.04 |
| Defoamer | Vegetable Oil | 0.3–0.4 |
| Moisturizer | Water | 90.0–93.9 |

The seed culture media is prepared in a container tank and stirred until completely homogeneous. The media is fed into a seed tank through a sieve. Water is added and the tank is closed. The tank is sterilized with steam and cooled. The seed media is inoculated and aeration and agitation is started. The air flow rate is from 0.5 to 2.0 m³ per minute per m³ fermentation broth. The temperature is held at 25° C. to 35° C. for 24 to 36 hours. The pH should be about 6.0, the amino nitrogen content should be from 60–120 mg/100 mL, and CTC potency should be greater than 75 u/mL.

Fermentation Media

The composition of the media for fermentation tanks will consists of the following ingredients and respective ranges. The media is prepared and transferred to the fermentation tank.

| Ingredient | Preferred Material | Preferred Range (%) |
|---|---|---|
| Carbon Source | Corn Starch | 7.0–9.0 |
| Nitrogen Source | Peanut Meal or Soybean Meal | 3.0–3.5 |
| Nitrogen Source | Peptone | 0.4–0.6 |
| Nitrogen Source | Yeast Powder | 0.4–0.8 |
| Bio-Catalyst | α-amylase | 0.01–0.02 |
| Nitrogen Source | $(NH_4)_2SO_4$ | 0.5–1.0 |
| Carbon Source & Buffer | $CaCO_3$ | 0.4–0.7 |
| Activator | $KH_2PO_4$ | 0.02–0.03 |
| Activator | NaCl | 0.1–0.3 |
| Activator | $MgSO_4$ | 0.01–0.03 |
| Nitrogen Source | Corn-Steep Liquor | 1.2–1.8 |
| Defoamer | Vegetable Oil | 0.15–.025 |
| Moisturizer | Water | 86.8–82.0 |

Sugar Tank Composition

The sugar preparation added to the fermentation tank during fermentation is composed of the following:

| Ingredient | Preferred Material | Preferred Range (%) |
|---|---|---|
| Carbon Source | Starch | 40–50 |
| Nitrogen Source | Peanut Meal or Soybean Meal | 0–0.6 |
| Nitrogen Source | Corn-Steep Liquor | 1.0–2.5 |
| Bio-Catalyst | α-amylase | 0.05–0.08 |
| Carbon Source & Buffer | $CaCO_3$ | 0.4–0.8 |
| Activator | NaCl | 0.2–0.4 |
| Nitrogen Source | Peptone | 0–0.3 |
| Nitrogen Source | Yeast Powder | 0–0.3 |
| Activator | $CaCl_2$ | 0–0.3 |
| Defoamer | Vegetable Oil | 0.15–.025 |
| Moisturizer | Water | 44.5–58.2 |

Air Used During the Production Process

Air used during the fermentation process should be purified prior to be being injected to the fermentation or other media. The air is drawn into a compressor through a filter consisting of metallic net and foam rubber. Any impurities in the air, such as dirt, dust, sand, etc., are then removed. The air from the compressor should be cooled to about 15° C. to about 35° C. The cooled air is then ridded of oil and water by passing through an oil and water separator. The air is then heated to about 40° C. to about 50° C. The air is then passed through a filtration system. The filtered air is then fed to the seed and fermentor tanks for use in aeration in the fermentation process.

The fermentation culture media is pumped from the compounding pool into the fermentor. The media is sterilized by the introduction of steam. After the fermentation media has cooled, the seed culture media is pumped into the fermentor through a sterile tube. Cultivation then takes place. During fermentation, the temperature is maintained at 25° C. to 35° C. for 120 to 140 hours, with sterilized sugar media added as required with aeration.

During fermentation, ammonia (20%) liquid is introduced into the fermentor as necessary to maintain pH at 5.5 to 6.3.

When potency reaches 15,000 u/mg (15%) or higher where a higher potency is desired, the fermentation process is ended and the fermentation broth is discharged into a clean storage tank. The harvested broth is pumped into the storage tank through a filter press. The wet cake is discharged from the filter press into trays for drying. The wet cake is dried in an oven by using hot air flow (or another suitable drying method). When the moisture content is less than about 6.0 percent, the drying is ended and the dried product is removed.

The dried product is milled and the product is passed through a 10 mesh screen. The semi-finished product is the crude chlortetracycline in a particulate form which has been passed through a 10 mesh screen.

Samples are drawn and analyzed for active ingredient content, moisture and ash content.

The premix product according to an exemplary embodiment of the present invention is prepared as follows. A semi-finished CTC product is found to have an active ingredient content of 10 to 45 percent. The semi-finished CTC fermentation product, mineral product (an exemplary embodiment utilizes limestone), and filler (an exemplary embodiment utilizes rice hulls) are placed in a blender in ratios of a sufficient quantity. An edible oil (an exemplary embodiment utilizes mineral oil) is sprayed over the carriers during the mixing process. Oil is added in a an amount of sufficient quantity to control dust. The resulting composition has an active ingredient concentration of approximately 10 to 45 percent.

Figure 2:
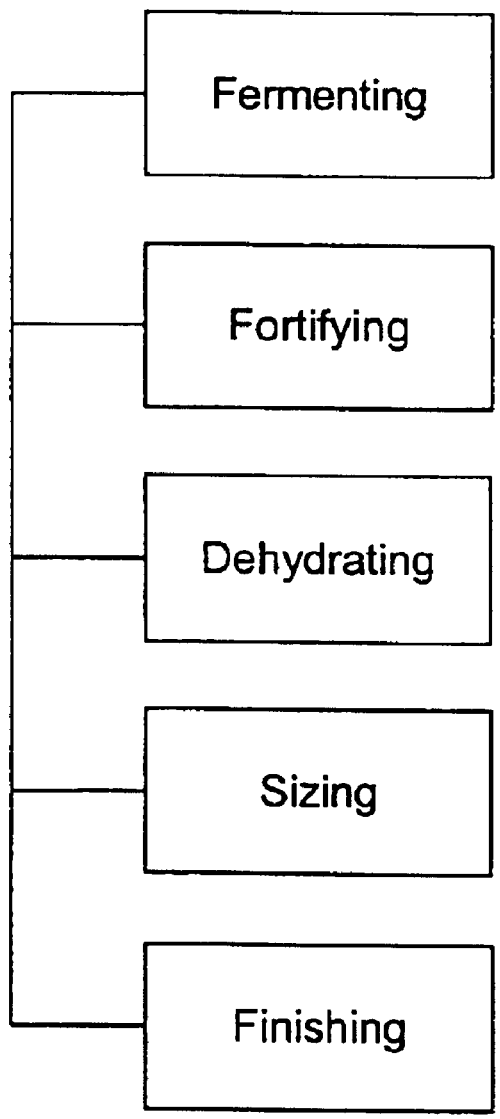
FIG. 2 is a diagrammatic illustration of an exemplary method of manufacturing a fortified particulate animal feed supplement of the present invention.

A preferred method for preparing a fortified particulate feed supplement is outlined in the diagram of FIG. 2. In a first embodiment, a fortified chlortetracycline composition is produced. To a chlortetracycline fermentation broth including the meal and liquid (for example, as resulting from a fermentation process substantially as described above) is added chlortetracycline in a pure or semi-pure form.

In one embodiment, the chlortetracycline added in a pure or semi-pure form may be a crude or partially recovered fermentation product from another fermentation batch. For example, a fermentation broth may be made acidic to form a readily soluble acid addition salt of chlortetracycline and the fermentation solids filtered out. The acid used may be any mineral acid or sufficiently strong organic acid as are known to those skilled in the art. Preferably, the acid is an acid that forms a pharmaceutically acceptable salt of chlortetracycline and most preferably is hydrochloric acid, sulfuric acid, or oxalic acid.

A filtrate from another fermentation batch containing chlortetracycline, or other pure or semi-pure source of chlortetracycline, may then be used to fortify the fermentation broth by addition thereto. The resulting product may then be dehydrated to a desired moisture content by separation of the liquid. The fortified fermentation broth may be further treated with a base prior to separating the liquid. The liquid separation may be by filtration, centrifuging, siphoning, decanting, pumping off, and so forth, form a wet cake which is further dried, until the moisture content reaches less than about 8% and preferably less than about 6%. The product is milled (e.g., by grinding and screening) to produce a granular product having the desired particle size, preferably about 10 mesh or larger. Particles larger than the desired size may be further milled. Particles smaller than the desired particle size may be collected and used in other applications, or may be recycled to the broth to further fortify chlortetracycline, concentration in subsequent batches.

In an alternative embodiment of the process of FIG. 2, the liquid chlortetracycline fortifying composition may be concentrated, for example, by drying, solvent extraction, adsorption onto a solid adsorbent, distillation, crystallization, and so forth, prior to being added to the fermentation broth.

In yet a further embodiment of the process of FIG. 2, the above described process may be varied by removing some or all of the liquid in the fermentation broth prior to the fortifying step. After liquid removal, the chlortetracycline in pure or semi-pure form is added to the fermentation solids. In this embodiment, the chlortetracycline in pure or semi-pure form will preferably be liquid, such as the filtrate from an acidified fermentation broth from another fermentation batch as described above.

In a second aspect of FIG. 2, a fortified oxytetracycline composition is produced. To an oxytetracycline fermentation broth including the meal and liquid (for example, as resulting from a fermentation process substantially as described above) is added oxytetracycline in a pure or semi-pure form.

In one embodiment, the oxytetracycline added in a pure or semi-pure form may be a crude or partially recovered fermentation product from another fermentation batch. For example, a fermentation broth may be made acidic to form a readily soluble acid addition salt of oxytetracycline and the fermentation solids filtered out. The acid used may be any mineral acid or sufficiently strong organic acid as are known to those skilled in the art. Preferably, the acid is an acid that forms a pharmaceutically acceptable salt of oxytetracycline and most preferably is hydrochloric acid, sulfuric acid, or oxalic acid.

A filtrate from another fermentation batch containing oxytetracycline, or other pure or semi-pure source of oxytetracycline, may then be used to fortify the fermentation broth by addition thereto. The resulting product may then be dehydrated to a desired moisture content by separation of the liquid. The fortified fermentation broth may be further treated with a base prior to separating the liquid. The liquid separation may be by filtration, centrifuging, siphoning, decanting, pumping off, and so forth, form a wet cake which is further dried, until the moisture content reaches less than about 8% and preferably less than about 6%., The product is milled (e.g., by grinding and screening) to produce a granular product having the desired particle size, preferably about 10 mesh or larger. Particles larger than the desired size may be further milled. Particles smaller than the desired particle size may be collected and used in other applications, or may be recycled to the broth to further fortify oxytetracycline concentration in subsequent batches.

In an alternative embodiment of the process of FIG. 2, the liquid oxytetracycline fortifying composition may be concentrated, for example, by drying, solvent extraction, adsorption onto a solid adsorbent, distillation, crystallization, and so forth, prior to being added to the fermentation broth.

In yet a further embodiment of the process of FIG. 2, the above described process may be varied by removing some or all of the liquid in the fermentation broth prior to the fortifying step. After liquid removal, the oxytetracycline in pure or semi-pure form is added to the fermentation solids. In this embodiment, the oxytetracycline in pure or semi-pure form will preferably be liquid, such as the filtrate from an acidified fermentation broth from another fermentation batch as described above.

Figure 3:
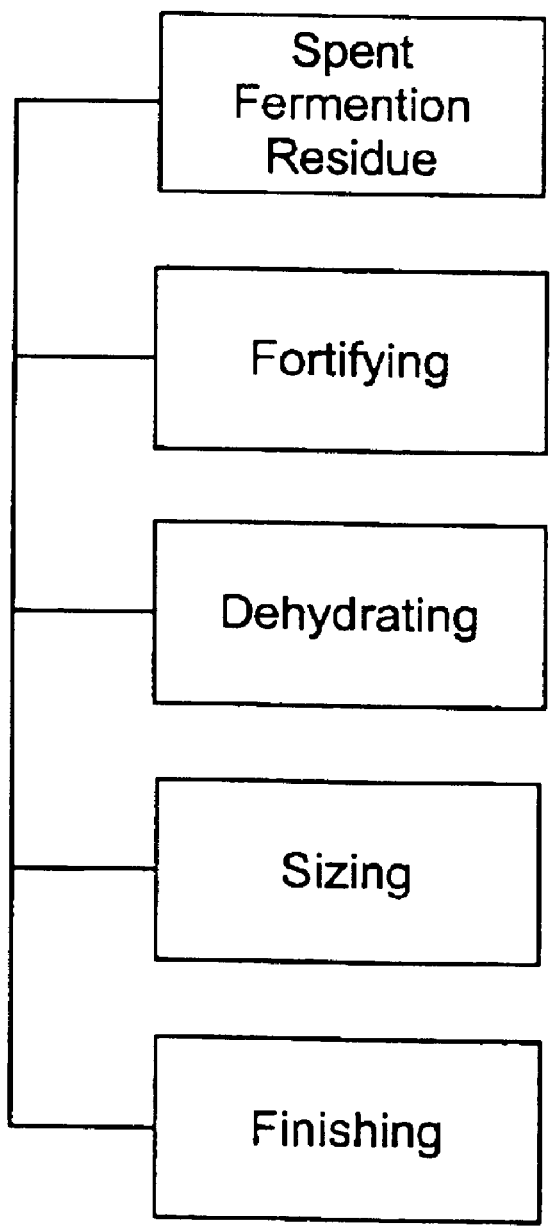
FIG. 3 is a diagrammatic illustration of another exemplary method of manufacturing a fortified containing particulate animal feed supplement of the present invention.
Figure 4:
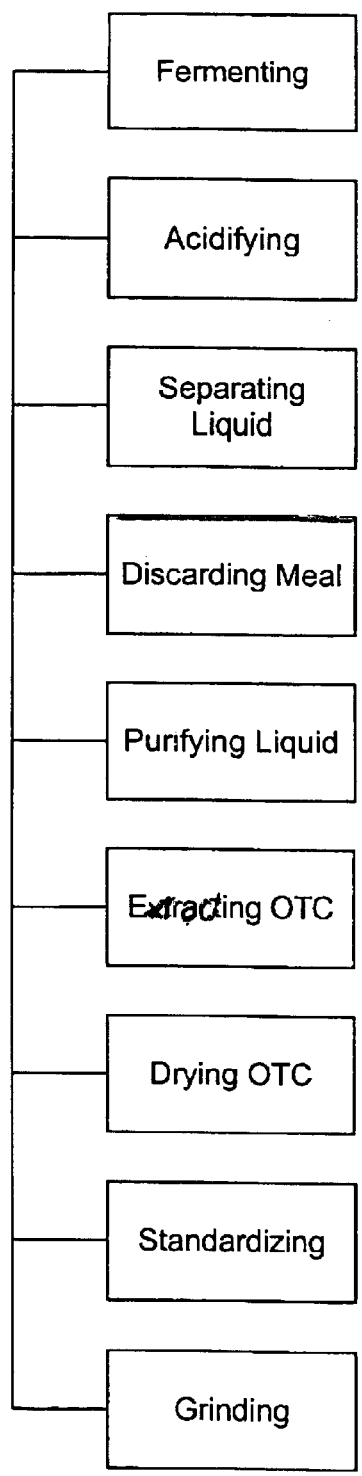
FIG. 4 is a diagrammatic illustration of a prior art method of manufacturing oxytetracycline feed supplements.

FIG. 3 illustrates a process according to the present invention wherein discarded meal (spent fermentation residue) from an oxytetracycline fermentation process may be used as the carrier to produce an oxytetracycline feed supplement. The spent fermentation residue may be that from a process generally of the type shown in FIG. 4. The fermentation residue having the oxytetracycline removed therefrom by acidification and removal of the liquid will have substantially no oxytetracyclin activity, although, the term "substantially" is not intended to preclude minor quantities that may remain after the liquid is separated.

To the spent fermentation residue is added oxytetracycline in a pure or semi-pure form (dry or liquid). In one embodiment, the oxytetracycline that is added in a pure or semi-pure form may be a crude or partially recovered fermentation product from another fermentation batch. For example, a fermentation broth may be made acidic to form a readily soluble acid addition salt of oxytetracycline to extract the oxytetracycline from the media to the liquid, and the fermentation solids filtered out. The acid used may be any mineral acid or sufficiently strong organic acid as are known to those skilled in the art. Preferably, the acid is an acid that forms a pharmaceutically acceptable salt of oxytetracycline and most preferably is hydrochloric acid, sulfuric acid, or oxalic acid.

A filtrate from another fermentation batch containing oxytetracycline, or other pure or semi-pure source of oxytetracycline, may then be used to fortify the fermentation broth by addition thereto. The resulting product may then be dehydrated to a desired moisture content by separation of the liquid. The fortified fermentation broth may be further treated with a base prior to separating the liquid. The liquid separation may be by filtration, centrifuging, siphoning, decanting, pumping off, and so forth, form a wet cake which is further dried, until the moisture content reaches less than about 8% and preferably less than about 6%. The product is milled (e.g., by grinding and screening) to produce a granular product having the desired particle size, preferably about 10 mesh or larger. Particles larger than the desired size may be further milled. Particles smaller than the desired particle size may be collected and used in other applications, or may be recycled to the broth to further fortify oxytetracycline concentration in subsequent batches.

In an alternative embodiment of the process of FIG. 3, the liquid oxytetracycline fortifying composition may be concentrated, for example, by drying, solvent extraction, adsorption onto a solid adsorbent, distillation, crystallization, and so forth, prior to being added to the fermentation broth.

In yet a further embodiment of the process of FIG. 3, the above described process may be varied by removing some or all of the liquid in the fermentation broth prior to the fortifying step. After liquid removal, the oxytetracycline in pure or semi-pure form is added to the fermentation solids. In this embodiment, the oxytetracycline in pure or semi-pure form will preferably be liquid, such as the filtrate from an acidified fermentation broth from another fermentation batch as described above.

All references cited herein are incorporated by reference in their entireties.

The description above should not be construed as limiting the scope of the invention, a but as merely providing illustrations to some of the presently preferred embodiments of this invention. In light of the above description and examples, various other modifications and variations will now become apparent to those skilled in the art without departing from the spirit and scope of the present invention as defined by the appended claims. Accordingly, the scope of the invention should be determined solely by the appended claims and their legal equivalents.

What is claimed is:

1. A substantially dustless animal feed premix composition in solid noncompacted granular form and having a resistance to powdering, said composition comprising a physical admixture of granular fermentation solids comprising an antibiotic and oil in an amount ranging from 0.01 to 10% based on the weight of said animal feed supplement, said fermentation solids resulting from reduction of a fermentation broth including a fermentation medium in which an organism was cultured for producing the antibiotic, said fermentation solids having an antibiotic activity sufficient to ameliorate an antibacterial infection to treat an animal wherein the antibiotic activity is at least 10 g/lb to 300 g/lb, and further comprising at least one potency standardizer selected from the group consisting of an edible feed material and mineral product.

2. A composition according to claim 1, wherein said antibiotic is chlortetracycline.

3. A composition according to claim 1, wherein said antibiotic is oxytetracycline.

4. A composition according to claim 1, wherein said mineral product is limestone.

5. A composition according to claim 4, wherein said edible feed material is rice hulls.

6. A particulate, substantially dustless noncompacted animal feed supplement comprising fermentation solids comprising an antibiotic product of a fermentation process, said fermentation solids resulting from reduction of a fermentation broth including a fermentation medium in which an organism was cultured for producing the antibiotic, said fermentation solids having an antibiotic activity sufficient to ameliorate an antibacterial infection to treat an animal wherein the antibiotic activity is at least 10 g/lb to 300 g/lb, said animal feed supplement prepared by blending fermentation solids with an edible feed material and a mineral product while spraying a non-toxic oil into said mixture during blending, wherein said non-toxic oil is added in an amount ranging from 0.001 to 11% based on the weight of said animal feed supplement into said material to produce a mixture thereof.

7. A particulate, substantially dustless noncompacted animal feed supplement comprising fermentation solids comprising an antibiotic product of a fermentation process, said fermentation solids resulting from reduction of a fermentation broth including a fermentation medium in which an organism was cultured for producing the antibiotic, said fermentation solids having an antibiotic activity sufficient to ameliorate an antibacterial infection to treat an animal wherein the antibiotic activity is at least 10 g/lb to 300 g/lb, said animal feed supplement prepared by blending fermentation solids with an edible feed material and a mineral product into said material to produce a mixture thereof, wherein said antibiotic is selected from the group consisting of tetracycline, chlortetracycline, demeclocycline, oxytetracycline.

8. An animal feed supplement according to claim 7, wherein said antibiotic is chlortetracycline.

9. An animal feed supplement according to claim 7, wherein said antibiotic is oxytetracycline.

10. A particulate, substantially dustless noncompacted animal feed supplement comprising fermentation solids comprising an antibiotic product of a fermentation process, said fermentation solids resulting from reduction of a fermentation broth including a fermentation medium in which an organism was cultured for producing the antibiotic, said fermentation solids having an antibiotic activity sufficient to ameliorate an antibacterial infection to treat an animal wherein the antibiotic activity is at least 10 g/lb to 300 g/lb, said animal feed supplement prepared by blending fermentation solids with an edible feed material and a mineral product into said material to produce a mixture thereof, wherein said mineral product is limestone.

11. An animal feed supplement according to claim 10, wherein said edible feed material is rice hulls.

12. A particulate, substantially dustless animal feed supplement comprising fermentation solids comprising an antibiotic product of a fermentation process, said animal feed supplement prepared by;
   culturing an organism producing an antibiotic selected from the group consisting of chlortetracycline and oxytetracycline in a fermentation medium to produce a fermentation broth comprising said antibiotic;
   adding an additional quantity of said antibiotic, said additional quantity of antibiotic being obtained from a fermentation broth, to the fermentation broth to increase the antibiotic activity of said fermentation broth;
   reducing said fermentation broth to obtain fermentation solids comprising said antibiotic;
   drying said fermentation solids to produce a solid having a low moisture content; and
   granulating said dried solid to produce granules having a substantially uniform particle size, said granulated fermentation solids having an antibiotic activity sufficient to ameliorate an antibacterial infection to treat an animal wherein the antibiotic activity is at least 10 g/lb to 300 g/lb.

13. A particulate, substantially dustless animal feed supplement comprising fermentation solids comprising an antibiotic product of a fermentation process, said animal feed supplement prepared by:
   culturing an organism producing an antibiotic in a fermentation medium to produce a fermentation broth comprising said antibiotic;
   adding an additional quantity of said antibiotic, said additional quantity of antibiotic being obtained from an fermentation broth, to the fermentation broth to increase the antibiotic activity of said fermentation broth, wherein said additional quantity of said antibiotic comprises a filtrate obtained from and acidified fermentation broth;
   reducing said fermentation broth to obtain fermentation solids comprising said antibiotic;
   drying said fermentation solids to produce a solid having a low moisture content; and
   granulating said dried solid to produce granules having a substantially uniform particle size, said granulated fermentation solids having an antibiotic activity sufficient to ameliorate an antibacterial infection to treat an animal wherein the antibiotic activity is at least 10 g/lb to 300 g/lb,
   wherein said additional quantity of said antibiotic is selected from the group consisting of chlortetracycline and oxytetracycline.

14. An animal feed supplement according to claim 13, wherein said additional quantity of said antibiotic comprises chlortetracycline calcium complex.

15. An animal feed supplement according to claim 13, wherein said additional quantity of said antibiotic comprises oxytetracycline calcium complex.

* * * * *